United States Patent
Hardouin et al.

(10) Patent No.: US 8,143,449 B2
(45) Date of Patent: Mar. 27, 2012

(54) PROCESS FOR THE SYNTHESIS OF AGOMELATINE

(75) Inventors: Christophe Hardouin, Le Havre (FR); Jean-Pierre Lecouve, Le Havre (FR)

(73) Assignee: Les Laboratoires Servier, Suresnes Cedex (FR)

( * ) Notice: Subject to any disclaimer, the term of this patent is extended or adjusted under 35 U.S.C. 154(b) by 471 days.

(21) Appl. No.: 12/462,360

(22) Filed: Aug. 3, 2009

(65) Prior Publication Data
US 2010/0036163 A1   Feb. 11, 2010

(30) Foreign Application Priority Data
Aug. 5, 2008   (FR) ...................... 08 04464

(51) Int. Cl.
C07C 233/05   (2006.01)
C07C 231/02   (2006.01)
(52) U.S. Cl. .................. 564/219; 564/139; 564/169
(58) Field of Classification Search .................. 564/139, 564/169, 219
See application file for complete search history.

(56) References Cited

FOREIGN PATENT DOCUMENTS
EP   0781764   7/1997
EP   1564202   8/2005

OTHER PUBLICATIONS

D. Becker, et al., "Ring opening of 3-methoxyacnaphthylene-1, 2-dione, Application of 13C-2D-*Inadequate*-N.M.R. spectroscopy to structure assignment of some substituted naphthlenes." Tetrahedron Letters, vol. 27, No. 32, p. 3775-3776, 1986.
French Preliminary Search Report for FR 0804464 of Mar. 12, 2009.

*Primary Examiner* — Shailendra Kumar
(74) *Attorney, Agent, or Firm* — Hueschen and Sage

(57) ABSTRACT

Process for the industrial synthesis of the compound of formula (I)

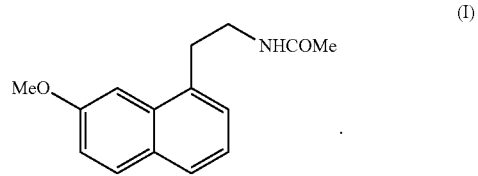

7 Claims, No Drawings

PROCESS FOR THE SYNTHESIS OF AGOMELATINE

The present invention relates to a new process for the industrial synthesis of agomelatine, or N-[2-(7-methoxy-1-naphthyl)ethyl]acetamide, of formula (I):

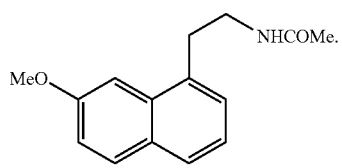
(I)

Agomelatine, or N-[2-(7-methoxy-1-naphthyl)ethyl]acetamide, has valuable pharmacological properties.

It has, in fact, the double characteristic of being, on the one hand, an agonist of receptors of the melatoninergic system and, on the other hand, an antagonist of the 5-HT$_{2C}$ receptor. These properties provide it with activity in the central nervous system and, more especially, in the treatment of major depression, seasonal affective disorder, sleep disorders, cardiovascular pathologies, pathologies of the digestive system, insomnia and fatigue due to jet-lag, appetite disorders and obesity.

Agomelatine, its preparation and its use in therapeutics have been described in European patent specifications EP 0 447 285 and EP 1 564 202.

In view of the pharmaceutical value of this compound, it has been important to be able to produce it using an effective industrial synthesis process which is readily transferable to the industrial scale and which provides agomelatine in a good yield and with excellent purity.

Patent specification EP 0 447 285 describes production of agomelatine in eight steps starting from 7-methoxy-1-tetralone, in an average yield of less than 30%.

In patent specification EP 1 564 202, the Applicant developed a new, much more effective and industrialisable synthesis route in only four steps starting from 7-methoxy-1-tetralone that makes it possible to obtain agomelatine in highly reproducible manner in a well-defined crystalline form.

However, the search for new synthesis routes, especially starting from starting materials that are less costly than 7-methoxy-1-tetralone, is currently still relevant.

The Applicant has continued his investigations and has developed a new process for the synthesis of agomelatine starting from 3-methoxyacenaphthoquinone: this new starting material has the advantage of being simple, readily obtainable in large quantities at less cost. 3-Methoxyacenaphthoquinone moreover also has the advantage of having a naphthalene ring system in its structure, which avoids inclusion of an aromatisation step into the synthesis, a step that is always problematic from an industrial point of view.

This new process moreover makes it possible to obtain agomelatine in reproducible manner and without requiring laborious purification, with a purity that is compatible with its use as a pharmaceutical active ingredient.

More specifically, the present invention relates to a process for the industrial synthesis of the compound of formula (I):

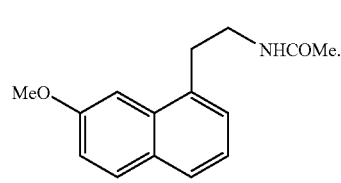
(I)

which process is characterised in that 3-methoxyacenaphthoquinone of formula (II):

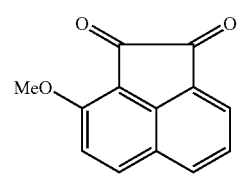
(II)

is reacted in the presence of a strong base to yield the compound of formula (III):

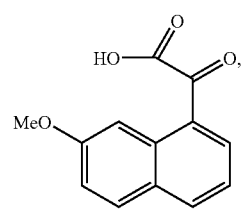
(III)

which is subjected to amination to yield the compound of formula (IV):

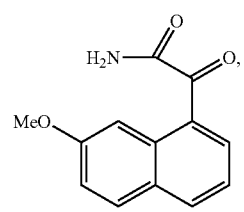
(IV)

which is subjected to the action of a reducing system to yield the compound of formula (V):

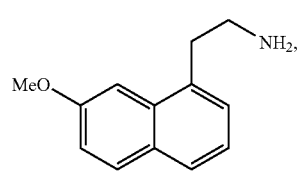
(V)

which is successively subjected to the action of sodium acetate and then acetic anhydride to yield the compound of formula (I), which is isolated in the form of a solid.

The compound of formula (II) is accessible to the person skilled in the art by means of conventional chemical reactions and/or chemical reactions described in the literature.

Advantageously, the conversion of the compound of formula (II) into the compound of formula (III) according to the invention is carried out using $NaNH_2$, $((CH_3)_3—Si)_2NLi$ (LiHMDS) or $((CH_3)_3—Si)_2NNa$ (NaHMDS).

The amination reaction is preferably carried out using $NH_4Cl$ and propylphosphonic anhydride.

As the reducing system in the conversion of the compound of formula (IV) into the compound of formula (V) according to the invention preference is given to $LiAlH_4$ or to the couple $BH_3.THF/AlCl_3$.

This process is especially valuable for the following reasons:
  it makes it possible to obtain the compound of formula (I) on an industrial scale in excellent yields, starting from a simple, low-cost starting material;
  it makes it possible to avoid an aromatisation reaction because the naphthalene ring system is present in the starting substrate;
  finally, the compound of formula (I) obtained has, in reproducible manner, the characteristics of the crystalline form described in patent specification EP1564202.

The compound of formula (IV) obtained according to the process of the invention is new and useful as an intermediate in the synthesis of agomelatine, wherein it is subjected to a reduction reaction, then to a coupling reaction with acetic anhydride.

The Examples hereinbelow illustrate the invention without limiting it in any way.

EXAMPLE 1

N-[2-(7-Methoxy-1-naphthyl)ethyl]acetamide

Step A: (7-Methoxy-1-naphthyl)(oxo)acetic acid

In a reactor, 4 mg of 18-crown-6 ether and then 230 mg of $NaNH_2$ are successively introduced into a suspension of 100 mg of 3-methoxyacenaphthoquinone in 1 ml of DMSO. The mixture is stirred for 30 minutes at ambient temperature. Water (2 ml) is then added, followed by 2N HCl solution (3 ml). After two extractions with ethyl acetate, the solvents are dried over $Na_2SO_4$ and then evaporated off to yield the title product in the form of a yellow solid in a yield of 88% and with a chemical purity of more than 94%.

Melting point: 99° C.

Step B: 2-(7-Methoxy-1-naphthyl)-2-oxoacetamide

In a reactor, 1 g of the compound obtained in Step A is introduced into 30 ml of acetonitrile, and there are then added 4.39 g of propylphosphonic anhydride and 438 mg of $NH_4Cl$ and, at the end of the addition, 3.8 ml of diisopropylamine at ambient temperature. The solution is stirred for 4 hours under nitrogen, the solvents are then evaporated off, the residue is taken up in saturated aqueous NaCl solution, and extraction with ethyl acetate is carried out. The solvents are then dried over $Na_2SO_4$ and then evaporated off to yield the title product in the form of an orange solid in a yield of 80% and with a chemical purity of 90%.

Melting point: 112° C.

Step C: 2-(7-Methoxy-1-naphthyl)ethanamine 480 mg of the compound obtained in Step B dissolved in THF (20 ml) are introduced into a reactor, followed by 2 eq. of $AlCl_3$ and finally, slowly, 6 eq. of $BH_3.THF$ solution, and the reaction mixture is stirred for 2.5 hours. Water (12 ml) is then added, followed by 25 ml of 1N sodium hydroxide solution together with 800 mg of solid sodium hydroxide, and three extractions with methyl tert-butyl ether (20 ml) are carried out. The solvents are then dried over $Na_2SO_4$ and then evaporated off to yield the title product in the form of a yellow oil in a yield of 80% and with a chemical purity of 95%.

Step D:
N-[2-(7-Methoxy-1-naphthyl)ethyl]acetamide

In a reactor, 5 g of the compound obtained in Step C and 2 g of sodium acetate are introduced into ethanol. The mixture is stirred, 2.3 g of acetic anhydride are then added, the reaction mixture is heated to reflux and 20 ml of water are added. The reaction mixture is allowed to return to ambient temperature and the precipitate obtained is filtered off, washed with an ethanol/water 35/65 mixture to yield the title product in a yield of 80% with a chemical purity of 99%.

Melting point: 108° C.

EXAMPLE 2

Determination of the Crystalline Form of the Compound
N-[2-(7-methoxy-1-naphthyl)ethyl]acetamide Obtained in Example 1

Data recording was carried out using the D8 high-resolution diffractometer from Bruker AXS with the following parameters: an angular range of 3°-90° in terms of 2θ, a step of 0.01° and 30 s per step. The N-[2-(7-methoxy-1-naphthyl)ethyl]acetamide powder obtained in Example 1 was deposited on a transmission mounting support. The X-ray source is a copper tube ($\lambda.CuK_{\alpha1}$=1.54056 Å). The mounting includes a front monochromator (Ge(111) crystal) and an energy-resolved solid-state detector (MXP-D1, Moxtec-SEPH). The compound is well crystallised: the line width at half-height is of the order of 0.07° in terms of 2θ.

The following parameters were accordingly determined:
crystal structure of unit cell: monoclinic
unit cell parameters: a=20.0903 Å, b=9.3194 Å, c=15.4796 Å, β=108.667°
space group: $P2_1/n$
number of molecules in the unit cell: 8
volume of the unit cell: $V_{Unit\ cell}$=2746.742 Å$^3$
density: d=1.13 g/cm$^3$.

EXAMPLE 3

Determination, by Means of the X-Ray Powder Diffraction Diagram, of the Crystalline Form of the N-[2-(7-methoxy-1-naphthyl)ethyl]acetamide Compound Obtained in Example 1

The crystalline form of the compound obtained in Example 1 is characterised by the following X-ray powder diffraction diagram, measured using a Siemens D5005 diffractometer (copper anticathode) and expressed in terms of interplanar distance d, Bragg's angle 2 theta, and relative intensity (expressed as a percentage in relation to the most intense line):

| Angle 2 theta (°) | Interplanar distance d (Å) | Intensity (%) |
|---|---|---|
| 9.26 | 9.544 | 23 |
| 10.50 | 8.419 | 13 |

-continued

| Angle 2 theta (°) | Interplanar distance d (Å) | Intensity (%) |
|---|---|---|
| 15.34 | 5.771 | 24 |
| 17.15 | 5.165 | 100 |

The invention claimed is:

1. A process for the synthesis of a compound of formula (I)

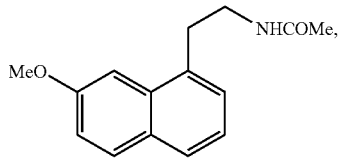
(I)

wherein 3-methoxyacenaphthoquinone of formula (II):

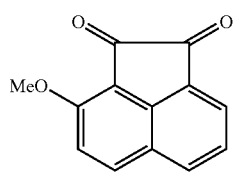
(II)

is reacted in the presence of a strong base to yield a compound of formula (III):

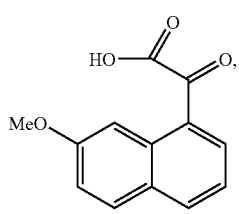
(III)

which is subjected to amination to yield a compound of formula (IV):

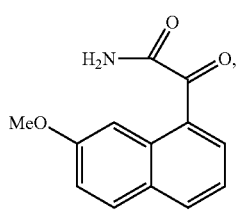
(IV)

which is subjected to the action of a reducing system to yield a compound of formula (V):

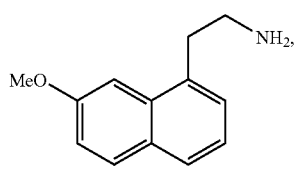
(V)

which is successively subjected to the action of sodium acetate and then acetic anhydride to yield the compound of formula (I), which is isolated in the form of a solid.

2. The process of claim 1, wherein the conversion of the compound of formula (II) into the compound of formula (III) is carried out using $NaNH_2$.

3. The process of claim 1, wherein the conversion of the compound of formula (IV) into the compound of formula (V) is carried out using the couple $BH_3.THF/AlCl_3$.

4. A compound of formula (IV)

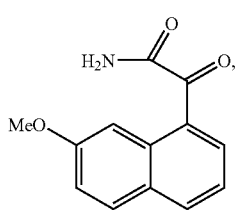
(IV)

for use as an intermediate in the synthesis of agomelatine.

5. A process for the synthesis of agomelatine of formula (I)

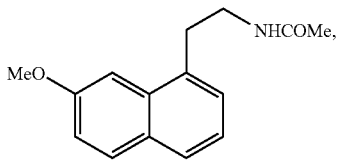
(I)

starting from a compound of formula (III) wherein the compound of formula (III) is obtained by the process of claim 1.

6. A process for the synthesis of agomelatine of formula (I)

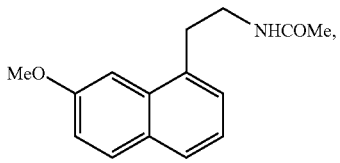
(I)

starting from a compound of formula (IV) wherein the compound of formula (IV) is obtained by the process of claim 1.

7. A process for the synthesis of agomelatine of formula (I)

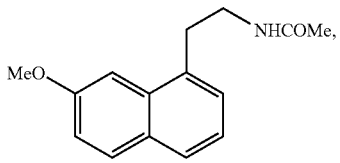
(I)

starting from a compound of formula (V) wherein the compound of formula (V) is obtained by the process of claim 1.

* * * * *